United States Patent [19]
Knebel et al.

[11] Patent Number: 6,040,473
[45] Date of Patent: Mar. 21, 2000

[54] PROCESS FOR THE PREPARATION OF POLYGLYCOL(METH)ACRYLATES

[75] Inventors: Joachim Knebel, Darmstadt; Werner Spalt, Weiterstadt, both of Germany

[73] Assignee: Roehm GmbH, Darmstadt, Germany

[21] Appl. No.: 09/101,761

[22] PCT Filed: Jan. 9, 1997

[86] PCT No.: PCT/EP97/00056

§ 371 Date: Jul. 20, 1998

§ 102(e) Date: Jul. 20, 1998

[87] PCT Pub. No.: WO97/26293

PCT Pub. Date: Jul. 24, 1997

[30] Foreign Application Priority Data

Jan. 20, 1996 [DE] Germany ............ 196 02 035

[51] Int. Cl.$^7$ ............................................. C07C 67/03
[52] U.S. Cl. ........................ 560/217; 560/221; 560/225
[58] Field of Search ................................ 560/217, 221, 560/225

[56] References Cited

U.S. PATENT DOCUMENTS

| 4,672,105 | 6/1987 | Schlosser et al. | 560/217 |
| 4,745,213 | 5/1988 | Schlosser et al. | 560/217 |
| 5,362,904 | 11/1994 | Kearns | 560/217 |

FOREIGN PATENT DOCUMENTS 4019788  1/1992  Germany.

*Primary Examiner*—Rosalynd Keys
*Attorney, Agent, or Firm*—Oblon, Spivak, McClelland, Maier & Neustadt, P.C.

[57] ABSTRACT

A transesterification process for the preparation of (meth) acrylates wherein a (meth)acrylic acid ester is re-esterified in the presence of a re-esterification catalyst comprised of calcium hydroxide or calcium hydroxide in combination with lithium chloride.

11 Claims, No Drawings

PROCESS FOR THE PREPARATION OF POLYGLYCOL(METH)ACRYLATES

FIELD OF THE INVENTION

The present invention relates to a process for the production of alkoxy polyglycol (meth)acrylates by basically catalyzed re-esterification, where a mixture of lithium chloride and calcium hydroxide or calcium hydroxide alone is used as the catalysts.

STATE OF THE ART

Esters of (meth)acrylic acid with polyethylene glycol, or the mono-ether derivatives of the same, are of quite some technical interest as monomers with a dispersant effect. It is all the more important to have as advantageous as possible a production method available.

Re-esterification of (meth)acrylic acid alkyl esters from lower alkanols. particularly of the methyl and ethyl esters with higher or with substituted alcohols. under catalysts with various catalysts, represents a relatively elegant method for the production of higher or more complex esters of (meth) acrylic acid.

Among the (meth)acrylic acid esters which are of interest because of their many different possibilities of use are those with alkoxy polyglycols.

While the re-esterification reaction of the stated, low (meth)acrylic acid esters with alkoxy polyglycols, for example under catalysts with the ortho-titanic acid esters which are used in the relevant literature (see GB 960 005; 962 928; DE-A 4 121 811) proceeds somewhat satisfactorily, processing of the re-esterification batches is extraordinarily difficult. While one obtains a product in good yield and with little inherent color under catalysts with tetraisopropyl titanate, for example, when the titanate is transformed into insoluble, hydratized titanium dioxide by adding water, which is unavoidable, a hydrolysis product is obtained which is extremely difficult to filter. The filtration process takes too much time to conduct the process on a production scale, so that processing can take days.

As an alternative to titanium catalysts, a possibility is catalysts by alkali alkoxides (CH-PS 239 750), for example, or with a certain lithium compound, particularly lithium hydroxide, preferably in combination with a catalyst that contains calcium oxide (see U.S. Pat. No. 4,672,105; U.S. Pat. No. 4,745,213; DE-A 2 744 641; GB-C 1 094 998).

TASK AND SOLUTION

In view of experience with the commonly used catalysts based on titanium, as explained above, there was a special need to have an effective and cost-effective re-esterification process available for the production of (meth)acrylic acid esters from polyethylene glycols, possibly mono-ethered.

However, corresponding experiments with the catalyst lithium hydroxide, or with the catalyst systems of lithium hydroxide and calcium hydroxide or lithium chloride and calcium oxide, which were very successfully used as alternatives to titanium catalysts, were disappointing. If, for example, methyl methacrylate is reacted with methoxypolyethylene glycol, under catalysts with the re-esterification catalysts mentioned, under the conditions which have otherwise proven themselves for other alcohols as edducts, products with a yellow to red-brown color are obtained, and they cannot be sold in this form.

(For the catalyst system of lithium hydroxide/calcium oxide, for example, the best yields were reported for reactions with polyols, in U.S. Pat. No. 4.672,105.) Therefore this type of re-esterification catalysts also appeared to be unsuitable for accomplishing the present task.

It was now found that the present task, that of making available a re-esterification process for the production of (meth)acrylic acid esters from polyethylene glycols and polypropylene glycols or their mono-ethers, which is satisfactory in every regard, can be accomplished according to the invention by using a catalyst system which consists of lithium chloride and calcium hydroxide or calcium hydroxide alone. The reaction products of these processes are characterized, among other things, in that if any discoloration does occur, it is practically insignificant. The good filterability of the batches should also be emphasized.

The present invention particularly relates to a re-esterification process for the production of (meth)acrylic acid esters of formula I

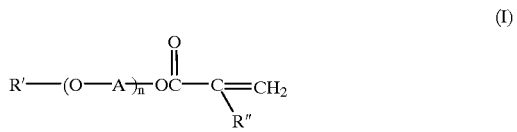

in which A stands for a radical selected from the group comprised of

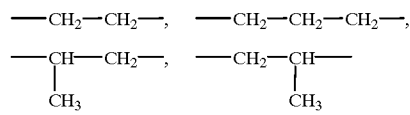

R' stands for a substituted alkyl radical, possibly branched, possibly with an aryl radical or an aryloxy radical, with 1 to 28 carbon atoms, or for a radical

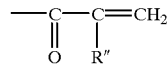

R" stands for hydrogen or methyl, and
n stands for a whole number from 2 to 250, particularly 2 to 50,
where a (meth)acrylic acid ester of formula II

in which R stands for a low alkyl radical, preferably C1–C4 alkyl radical, and R" has the meaning indicated above,
is re-esterified with the alcohol of formula III

in which R'" stands for hydrogen or for the R' radical, and A and n have the meanings indicated above, in the presence of a re-esterification catalyst comprised of lithium chloride and calcium hydroxide or calcium hydroxide alone.

An aryl radical or an aryloxy radical as the substifuent in R' should be particularly understood as being a phenyl or phenoxy radical.

It is practical to use the re-esterification catalyst comprised of lithium chloride and possibly calcium hydroxide in catalytic amounts, in general 0.01 to 10 wt.-%, preferably 0.2 to 5 wt.-% with reference to the alcohols of formula III which are used. In this connection, the proportion of lithium chloride in the total catalyst is 0 to 50 wt.-%, preferably 0 to 30 wt.-%. As a guideline value, for example, a catalyst composition of 20 wt.-% lithium chloride and 80 wt.-% calcium hydroxide should be mentioned, with an application amount of 0.25 wt.-% with reference to the total weight of the reaction batch.

It is practical if the (meth)acrylic acid ester of formula II is present in excess above the stoichiometrically calculated amount, in each instance dependent on whether the alcohols of formula III represent a diol or its mono-ether. In general, an approximately 1.5 to 10 times excess above the calculated amount is used—as a guideline value, an approximately 5 times excess of ester of formula III above the alcohol of formula II will be mentioned. The use of methyl methacrylate or methyl or ethyl acrylate is preferred. The alcohols of formula III comprise, for example, tetraethylene glycol as well as the polyethylene glycols in the molecular weight range of 380 to approximately 9000.

In general, it is not necessary to also use a solvent. If necessary, however, inert solvents (those not forming radicals), such as hydrocarbons such as toluene, cyclohexane, hexane, heptane, and the like can be used.

It is urgently recommended that at least one stabilizing agent of the radical scavenger type also be used, in order to stop polymerization of the compounds capable of polymerization which are present in the reaction batch.

Representatives of the group of hydroquinones, sterically inhibited phenols, and sterically inhibited amines as well as hydroxylamine derivatives should be mentioned (see Ullmann's Encyclopedia of Industrial Chemistry, Vol. A 20, 460–505 VCH 1992).

The presence of representatives of at least two groups, for example of the hydroquinone compounds such as, for example, hydroquinone monomethyl ether, of the sterically inhibited phenols such as, for example, 4-methyl 2,6,-di-tert-butyl phenol, 2,4-dimethyl-6-tert-butyl phenol, of the sterically inhibited amines such as 4-hydroxy-2,2,6,6,-tetramethyl piperidinooxyl, as well as of the hydroxylamine compounds such as N,N-diethyl hydroxylamine, has proven to be advantageous. In general, these stabilizing agents are used in the ppm range, for example in the range of 50–5000 ppm with reference to the total of the components present. It has proven to be particularly advantageous, after the completion of alcoholysis, to add a compound of the silica type, possibly because of a certain base binding capacity. The amounts are preferably in the range of 1 to 2 times the amount of catalyst used.

It is practical to conduct the reaction above room temperature, preferably in the range of 60–120° C. If methyl methacrylate or methyl acrylate, which are especially preferred, is used, it is practical to draw the methanol in the azeotropic mixture, which is formed during re-esterification, off with the methacrylic acid ester (at 65–75° C.).

The reaction time is generally 1–20, preferably 3–5 hours. The reaction can be conducted as follows:

The multi-valent alcohol or its mono-ether of formula III are presented in a suitable reaction vessel with the excess of the (meth)acrylic acid ester and the stabilizer. The catalyst can be added during the reaction, or it is present right from the start. If it is added to the reaction mixture, it is recommended that it be added into the mixture in microfine form, for example as powder or granulate.

The reaction can take place as follows, for example:

The mixture of the alcohol of formula III, the low (meth)acrylic acid ester of formula II in excess, the stabilizers, the catalyst composed of lithium chloride plus calcium hydroxide or calcium hydroxide alone is presented in a suitable reactor with a stirrer device, for example a 20 liter VA vessel with a double-anchor stirrer device, with controlled air supply and steam heating, equipped with a distillation column, column head (liquid phase separator) cooler and recipient.

The re-esterification reaction preferably takes place within a total reaction time of approximately 4–5 hours and at a sump temperature in the range of >100° C. and <120° C., for example <105° C., particularly at 110–118° C.

After completion of alcoholysis, the silica compound is added at approximately 80° C. and the mixture is stirred for a short period of time, for example 10 minutes. It is practical if the crude ester solution is subjected to filtration, for example by means of a 2 l Seitz pressure filter. The filtration process generally proceeds without any problems. It is then advantageous to evaporate the solution in a thin-layer evaporator and subsequently dilute it to a desired concentration with water.

The substances are generally obtained in the form of a slightly yellowish, viscous liquid which solidifies to a white, wax-like mass at room temperature. When mixed with water, an almost colorless, clear ester of formula I is obtained, for example, if necessary after an additional filtration process.

The (meth)acrylic acid esters of formula I which can be obtained according to the invention have a broad spectrum of possible uses as (co)monomers. For example, their dispersant properties in the absence of basic groups containing nitrogen should be mentioned.

The following examples illustrate the process according to the invention.

EXAMPLE 1

Production of methoxypolyethylene glycol-750-methacrylate 9 kg (12 moles) methoxypolyethylene glycol-750, 6 kg (60 moles) methyl methacrylate, 7.5 g lithium chloride, and 30 g calcium hydroxide are presented in a 20l stainless steel vessel with double-anchor stirrer, air feed pipe, 1 m NW50 glass column filled with packages from the Sulzer company, Type EX, and automatic column head (liquid phase separator), cooler and recipient. 0.81 g hydroquinone monomethyl ether, 6.1 g 2,6-di-tert-butyl-4-methyl phenol and 1 g N,N-diethyl hydroxylamine are added as inhibitors.

While feeding in air, the reaction mixture is heated to 110–118° C. and, at the same time, a methyl methacrylate/methanol azeotrope is drawn off via the column head, until the head temperature reaches 99° C. after 4.5 h, and alcoholysis is complete. The mixture is cooled to 80° C. and 45 g Tonsil L80 FF (Südchemie AG) are added. After 10 min of stirring, the reaction mixture is pressure-filtered and excess methyl methacrylate is removed in a thin-layer evaporator DS 50 (NGW=Normschliff Gerätebau Wertheim) at 95° C. and 12 mbar. 9.7 kg methoxypolyethylene glycol-750-methacrylate are obtained as a yellowish, viscous liquid, which solidifies into a wax-like mass at room temperature. The product possesses a color number of 20, according to APHA, in a 50% aqueous solution.

EXAMPLE 2

Methacrylic acid ester of a fatty alcohol ethoxylate

Carried out as in Example 1, but using 9.5 kg (7 moles) Lutensol® AT25 (BASF, reaction product of a $C_{16}$–$C_{18}$ fatty alcohol mixture with 25 moles ethylene oxide), 7 kg (70 moles) methyl methacrylate, 6.5 g lithium chloride, and 25.9 g calcium hydroxide. 1.75 g hydroquinone monomethyl ether and 0.175 g diethyl hydroxylamine are added as inhibitors.

Alcoholysis is carried out in 5.75 h at sump temperature of 109–114° C. After the end of the reaction, the mixture is cooled to 45° C. and 64.7 g Tonsil L80 FF (Südchemie AG) are added. After 10 min of stirring, the reaction mixture is mixed with 5 kg MMA and pressure-filtered at the same temperature, after 130 g diatomaceous earth Seitz-Super (Seitz) are first added. The filtrate is mixed with 19 kg methyl methacrylate. 30 kg of a 25% solution of the methacrylic acid ester of Lutensol® AT 25 are obtained, with a color number of 14 and a hydroxyl number of <0.1.

EXAMPLE 3

Production of methoxypolyethylene glycol-750-methacrylate 555 g (0.75 mole) methoxypolyethylene glycol-750, 370 g (3.7 moles) methyl methacrylate, and 4.9 g calcium hydroxide are presented in a 2 l round flask with a mechanical stirrer, air feed pipe, 50 cm column NS 29 filled with laboratory packages from the Sulzer company, Type EX, and automatic column head (liquid phase separator), cooler and recipient. 0.063 g hydroquinone monomethyl ether, 0.063 g 2,6-di-tert-butyl-4-methyl phenol and 0.126 g diethyl hydroxylamine are added as inhibitors. While feeding in air, the reaction mixture is heated to 113–122° C. and, at the same time, a methyl methacrylatel-methanol azeotrope is drawn off via the column head, until the head temperature reaches 99° C. after 3.75 h, and alcoholysis is complete. The crude ester solution obtained is condensed in a rotation evaporator (75° C. water bath, 100 . . . 3 mbar pressure) and subsequently adjusted to a 50% solution of the methoxypolyethylene glycol-750-methacrylate by adding 605 g water. Subsequently, the solution is pressure-filtered. 575 g of a 50% solution of the product in water are obtained, with a color number of 45, according to APHA.

We claim:

1. Process for the production of (meth)acrylic acid esters of formula I

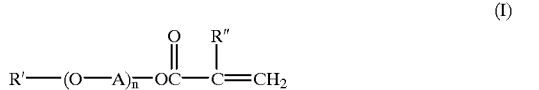

(I)

in which A stands for a radical selected from the group consisting of

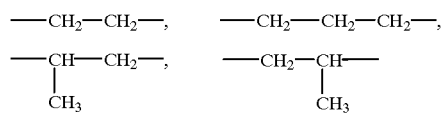

R' stands for a straight-chain or branched alkyl radical, optionally substituted with an aryl radical or an aryloxy radical, with 1 to 28 carbon atoms, or for a radical

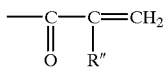

R" stands for hydrogen or methyl, and n stands for a whole number from 2 to 250, in a re-esterification reaction, characterized in that a (meth)acrylic acid ester of formula II

(II)

in which R stands for a lower alkyl radical, and R" has the meaning indicated above, is re-esterified in the presence of a re-esterification catalyst comprised of calcium hydroxide ($Ca(OH)_2$) or calcium hydroxide in combination with lithium chloride, with an alcohol of formula III

(III)

in which R'" stands for hydrogen or for the radical R' radical, and A and n have the meanings indicated above.

2. Process according to claim 1, characterized in that R in formula II stands for methyl, ethyl, or butyl.

3. Process according to claim 1, characterized in that re-esterification is carried out in the presence of at least one known stabilizer.

4. Process according to claim 3, characterized in that the stabilizer is selected from the group consisting of hydroquinone compounds, sterically inhibited phenols, sterically inhibited amines and hydroxylamine derivatives.

5. Process according to claim 1, characterized in that the stabilizing agents are used in amounts of 50–5000 ppm.

6. Process according to claim 1, characterized in that the (meth)acrylic acid esters of formula II are used in a 1.5 to 10 times excess as compared with the alcohols of formula III.

7. Process according to claim 1, characterized in that the re-esterification catalyst comprised of calcium hydroxide and optionally lithium chloride is used in amounts of 0.01 to 10 wt.-% with reference to the alcohol of formula III.

8. Process according to claim 1, characterized in that the weight ratio of lithium chloride to calcium hydroxide lies in the range from 0 to 100 to 50 to 50.

9. Process according to claim 1, characterized in that re-esterification is carried out while heating.

10. Process according to claim 8, characterized in that re-esterification is carried out at least partially in the temperature range of >100° C. to <120° C.

11. Process according to claim 1, characterized in that the reaction mixture is subjected to filtration after completion of re-esterification.

* * * * *

UNITED STATES PATENT AND TRADEMARK OFFICE
CERTIFICATE OF CORRECTION

PATENT NO. : 6,040,473

DATED : March 21, 2000

INVENTOR(S): Joachim KNEBEL et al.

It is certified that an error appears in the above-identified patent and that said Letters Patent is hereby corrected as shown below:

On the title page, item [75], the 1st Inventor's city is erroneously listed. It should read as follows:

--[75] Inventors: Joachim Knebel, Alsbach-Haehnlein; Werner Spalt, Weiterstadt, both of Germany--

Signed and Sealed this

Tenth Day of April, 2001

*Attest:*

NICHOLAS P. GODICI

*Attesting Officer*  *Acting Director of the United States Patent and Trademark Office*